United States Patent

Stock

[11] Patent Number: 5,866,794
[45] Date of Patent: Feb. 2, 1999

[54] DEVICE FOR CALIBRATING A GAS METER

[75] Inventor: Burkhard Stock, Lübeck, Germany

[73] Assignee: Drägerwerk Aktiengesellschaft, Lübeck, Germany

[21] Appl. No.: 796,515

[22] Filed: Feb. 6, 1997

[30] Foreign Application Priority Data

May 15, 1996 [DE] Germany .................. 196 19 673.6

[51] Int. Cl.⁶ .................. G01N 21/61; G01N 27/27
[52] U.S. Cl. .................. 73/1.06; 250/252.1; 204/401
[58] Field of Search .................. 73/1.06; 250/252.1 A; 204/401

[56] References Cited

U.S. PATENT DOCUMENTS

| | | | |
|---|---|---|---|
| 4,793,173 | 12/1988 | Moreth et al. | 73/1.03 |
| 5,394,730 | 3/1995 | Crozier | 73/1.06 |
| 5,493,891 | 2/1996 | Slemeyer | 73/1.06 |
| 5,612,896 | 3/1997 | Stock | 702/24 |
| 5,720,906 | 3/1998 | Matthiessen et al. | 73/19.01 |

FOREIGN PATENT DOCUMENTS 35 21 535 C1  9/1986  Germany .
43 44 196 A1  6/1995  Germany .

*Primary Examiner*—Thomas P. Noland
*Attorney, Agent, or Firm*—McGlew and Tuttle

[57] ABSTRACT

A device for calibrating a gas meter, in which gas to be analyzed is introduced into a measuring chamber by a delivery device via a delivery line. A storage tank is provided containing a calibrating substance, which tank is connected to the measuring chamber via a feed line. The storage tank is designed as a tank through which the gas to be analyzed can flow and has a gas inlet. A flow divider is provided in the course of the delivery line. A partial flow of the gas to be analyzed is sent by the flow divider to the gas inlet via a section of the feed line. The gas meter is an electrochemical measuring cell determining a measured concentration value of the calibrating substance in the gas to be analyzed in the measuring chamber. An infrared meter is provided, which evaluates the gas to be analyzed in the measuring chamber and generates a reference measured concentration value for the measured concentration value determined with the electrochemical measuring cell.

7 Claims, 1 Drawing Sheet

U.S. Patent   Feb. 2, 1999   5,866,794
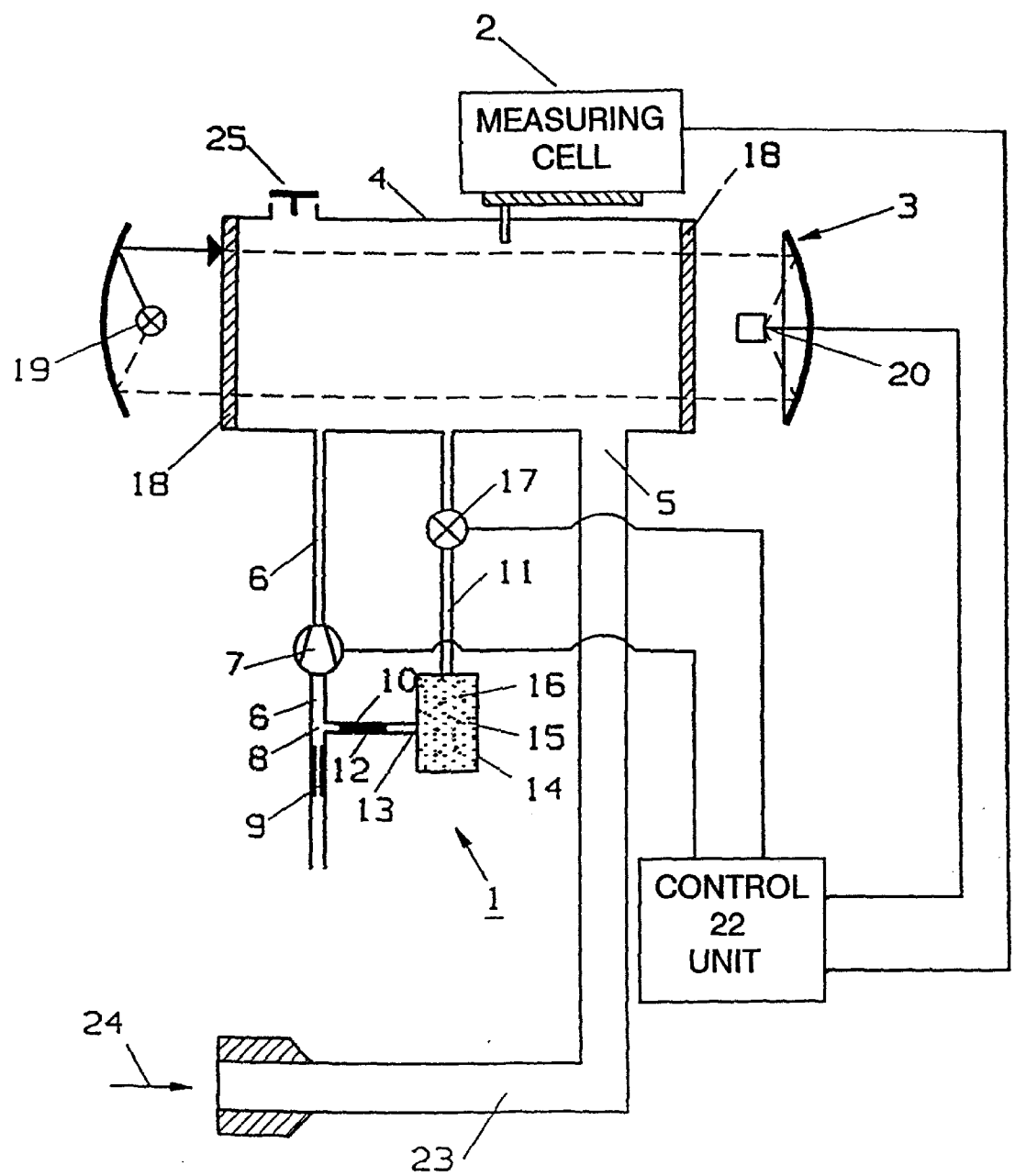

DEVICE FOR CALIBRATING A GAS METER

FIELD OF THE INVENTION

The present invention pertains to a device for calibrating a gas meter, in which gas to be analyzed is introduced into a measuring chamber by a delivery device via a delivery line and with a storage tank containing a calibrating substance which is connected via a feed line and to a process for calibrating the device.

BACKGROUND OF THE INVENTION

A device for calibrating a gas meter, in which gas to be analyzed is pumped by means of a delivery device from a gas inlet to a gas outlet of a measuring chamber, has been known from DE 35 21 535. To generate a calibrating gas mixture, a defined amount of liquid calibrating substance is delivered with a metering pump from a storage tank into the measuring chamber. The calibrating substance evaporates there and mixes with a purge gas present in the measuring chamber to form a calibrating gas of a predetermined composition. The mixing of the calibrating substance is facilitated by a heater located in the measuring chamber and the convection caused by it within the measuring chamber.

The drawback of the prior-art device is that an expensive pump is needed for the accurate metering of the calibrating substance in order to set a defined percentage of the calibrating substance in the gas to be analyzed. In addition, stable temperature conditions must prevail in the measuring chamber, which cannot be ensured without difficulties in the case of portable meters, which must be small and compact.

A process for determining certain characteristics of a substance that can be caused to engage in electrochemical reactions in a gas sample was disclosed in DE 43 44 196. It was found that the sensor current curves of the electrochemical gas-measuring cell have different rates of reaction for different alcohols. Thus, the rate of reaction for methanol in the measuring cell is only one fifth that for ethanol. Identification of the substance present is possible based on the different rates of reaction.

SUMMARY AND OBJECTS OF THE INVENTION

The primary object of the present invention is to provide a simple calibrating device for an electrochemical measuring cell.

According to the invention, a device for calibrating a gas meter is provided. Gas to be analyzed is introduced into a measuring chamber by a delivery means via a delivery line. A storage tank is provided containing a calibrating substance which is connected via a feed line. The storage tank has a gas inlet and is designed as a tank through which the gas to be analyzed can flow, wherein the gas to be analyzed is enriched with the calibrating substance within the storage tank. The gas meter is an electrochemical measuring cell determining a measured concentration value of the calibrating substance in the gas to be analyzed in the measuring chamber. An infrared meter is provided, which evaluates the gas to be analyzed in the measuring chamber and generates a reference measured concentration value for the measured concentration value determined with the electrochemical measuring cell.

The advantage of the present invention is essentially that an electrochemical measuring cell is calibrated in such a way that a calibrating substance is introduced into a measuring chamber, in which the gas species composition is continuously monitored by an infrared meter. Calibration of the electrochemical measuring cell is possible by determining a reference concentration value with the infrared meter. It is not necessary to impose any special requirements on the source of the calibrating gas because of the reference measurement. The calibrating gas is admitted into the measuring cell until a predetermined concentration is determined with the infrared meter. The feed of calibrating gas into the measuring cell is then interrupted, and the concentration measurement is performed with the electrochemical measuring cell, which takes a gas sample from the measuring cell. The present invention can be used especially advantageously in connection with the analysis of breath alcohol.

A flow divider is preferably provided in the course of the delivery line, by which a partial flow of the gas to be analyzed is sent over a section of the feed line to the gas inlet. The flow divider preferably comprises a first flow resistance and a branch-off point connecting the section of the feed line to the delivery line. The branch-off point is preferably arranged in front of the first flow resistance in the direction of the arriving flow.

The delivery means is preferably connected to a gas outlet of the measuring chamber as part of the delivery line, and the flow divider is provided in the course of the line of the gas outlet. The storage tank is provided with a porous storage material for a liquid calibrating substance. A second flow resistance is preferably provided in the section of the feed line leaving the branch-off point. A valve interrupting the flow of gas through the storage tank may be present in the course of the feed line.

An advantageous process for calibrating a gas meter, which has a measuring chamber with an infrared meter and with an electrochemical measuring cell, comprises purging the measuring chamber first with an inert gas, e.g., ambient air, introducing a calibrating gas flow containing a calibrating substance into the measuring chamber and monitoring the percentage of the calibrating substance in the gas flow with the infrared meter, interrupting the feed of calibrating substance when the percentage of the calibrating substance has reached a predetermined value, determining the percentage of calibrating substance in the measuring chamber as a measured concentration value with the electrochemical measuring cell, and using the measured value determined with the infrared meter as a reference measured concentration value for the measured concentration value.

The predetermined percentage of calibrating substance in the measuring chamber advantageously corresponds to the percentage of the component, e.g., breath alcohol, which was admitted into the measuring chamber before.

One exemplary embodiment is shown in the drawing and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a schematic sectional view of a device 1 for calibrating an electrochemical measuring cell.

DESCRIPTION OF THE PREFERRED EMBODIMENT

Referring to the drawings in particular, the only FIGURE schematically shows a device 1 for calibrating an electrochemical measuring cell 2 by means of an infrared gas meter 3 as a reference meter. The device 1 comprises a measuring chamber 4, which receives a gas to be analyzed and has a first section 5 of a delivery line as a gas inlet and a second section 6 of a delivery line as a gas outlet, hereinafter called the gas inlet 5 and the gas outlet 6. A delivery means 7 (e.g. a pump), a branch-off point 8, and a capillary 9 as a first flow resistance are located in the course of the gas outlet 6, and the gas to be analyzed, which is present in the measuring chamber 4, is pumped by means of the delivery means 7 from the gas inlet 5 to the gas outlet 6, and the branch-off point 8 is located on the flow arrival side of the capillary 9. Due to the dynamic pressure building up in front of the capillary 9, a partial flow of the gas flow being delivered enters, via a section 10 of a feed line 11 and a capillary 12 acting as a second flow resistance into a gas inlet 13 of a storage tank 14, which is filled with a porous storage material 15, which receives a liquid calibrating substance 16. The calibrating substance 16 is ethanol in this case. The partial flow flowing through the storage tank 14 returns into the measuring chamber 4 via the feed line 11 and a valve 17 located in the feed line 11. The measuring chamber 4 has transparent windows 18, which are transparent to infrared radiation. An infrared radiation source 19 and an infrared detector 20, which together are parts of the infrared gas meter 3 and analyze the gas within the measuring chamber 4, are located on both sides of the windows 18. The infrared gas meter 3, the electrochemical measuring cell 2, the delivery means 7, and the valve 17 are connected to a control and evaluation unit 22. The gas inlet 5 is connected to a breathing tube 23, into which the subject, not shown in the FIGURE, blows in the direction of the arrow 24. The gas exhaled by the subject into the measuring chamber 4 can escape from the measuring chamber 4 via a nonreturn valve 25. The device 1 according to the present invention is used to analyze breath alcohol.

The measurement process of the breath gas analysis is as follows:

A subject, whose breath gas contains alcohol, blows through the breathing tube 23 into the measuring chamber 4 and, via the nonreturn valve 25, into the environment. The breath gas sample is first analyzed for its alcohol content with the electrochemical measuring cell 2 in the known manner. The measured value determined with the electrochemical measuring cell 2 is stored as a measured concentration value in the control unit 22. The delivery means 7 is started during the subsequent calibration, and the measuring chamber 4 is first purged with ambient air, which is drawn in via the gas inlet 5 and the breathing tube 23. The valve 17 is then opened, and the measuring chamber is gradually filled with the calibrating substance 16 present in the storage tank 14. The concentration of the calibrating substance 16 in the measuring chamber 4 is continuously measured with the infrared meter 3 until the measured concentration value previously determined for the subject is reached. The delivery means 7 is then switched off, and the percentage of calibrating substance in the measuring chamber 4 is determined with the electrochemical measuring cell. The measured concentration value determined before with the infrared meter 3 is used as a reference measured concentration value for the measured value that was determined with the electrochemical measuring cell. By evaluating the current curve of the electrochemical measuring cell, identification of the alcohol exhaled by the subject is also possible. The current curve of the calibrating substance can thus be compared with the current curve that was obtained at the time of the analysis of the gas exhaled by the subject. The measurement is discarded in the case of unacceptable deviations. The comparison of the current curves may be performed, e.g., analogously to the process described in DE 43 44 196. Performing the calibration at the concentration that was obtained during the breath gas analysis of the subject is particularly advantageous here. Phenomena of aging of the electrochemical measuring cell and nonlinearities of the curve can thus be eliminated.

While a specific embodiment of the invention has been shown and described in detail to illustrate the application of the principles of the invention, it will be understood that the invention may be embodied otherwise without departing from such principles.

What is claimed is:

1. A device for calibrating a gas meter, comprising:

a measuring chamber in which gas to be analyzed is introduced;

delivery means for introducing gas to be analyzed into said measuring chamber via a delivery line;

a storage tank containing a calibrating substance;

a feed line connecting said storage tank with said measuring chamber, said storage tank having a gas inlet and defining a tank through which the gas to be analyzed can flow, wherein the gas to be analyzed is enriched with said calibrating substance within said storage tank;

an electrochemical measuring cell as said gas meter for determining a measured concentration value of the calibrating substance in the gas to be analyzed in said measuring chamber; and an infrared meter, which evaluates the gas to be analyzed in said measuring chamber and generates a reference measured concentration value for the measured concentration value determined with said electrochemical measuring cell.

2. A device in accordance with claim 1, further comprising: a flow divider provided in the course of said delivery line, by which a partial flow of the gas to be analyzed is sent over a section of said feed line to said gas inlet.

3. A device in accordance with claim 2, wherein said flow divider comprises a first flow resistance and a branch-off point connecting said section of said feed line to said delivery line, and that a branch-off point is arranged in front of said first flow resistance in a direction of arriving flow.

4. A device in accordance with claim 3, further comprising: a second flow resistance provided in said section of said feed line leaving said branch-off point.

5. A device in accordance with claim 2, wherein said delivery means is connected to said gas outlet of said measuring chamber as part of said delivery line, and said flow divider is provided in a course of the line of said gas outlet.

6. A device in accordance with claim 1, wherein said storage tank is provided with a porous storage material for a liquid calibrating substance.

7. A device in accordance with claim 1, further comprising a valve interrupting the flow of gas through the storage tank, said valve being disposed in the course of said feed line.

* * * * *